US011304590B2

(12) United States Patent
Krivopisk et al.

(10) Patent No.: US 11,304,590 B2
(45) Date of Patent: Apr. 19, 2022

(54) ILLUMINATOR CIRCUIT BOARD ASSEMBLY FOR AN ENDOSCOPE

(71) Applicant: EndoChoice, Inc., Alpharetta, GA (US)

(72) Inventors: Leonid Krivopisk, Nesher (IL); Amram Aizenfeld, Ramot Menashe (IL)

(73) Assignee: EndoChoice, Inc., Alpharetta, GA (US)

( * ) Notice: Subject to any disclaimer, the term of this patent is extended or adjusted under 35 U.S.C. 154(b) by 0 days.

(21) Appl. No.: 16/892,802

(22) Filed: Jun. 4, 2020

(65) Prior Publication Data

US 2020/0297191 A1 Sep. 24, 2020

Related U.S. Application Data

(63) Continuation of application No. 15/610,201, filed on May 31, 2017, now abandoned, which is a continuation-in-part of application No. 15/411,103, filed on Jan. 20, 2017, now Pat. No. 10,517,464, which is a continuation-in-part of application No.
(Continued)

(51) Int. Cl.
| | |
|---|---|
| *A61B 1/05* | (2006.01) |
| *A61B 1/06* | (2006.01) |
| *A61B 1/00* | (2006.01) |
| *A61B 1/018* | (2006.01) |
| *A61B 1/12* | (2006.01) |

(Continued)

(52) U.S. Cl.
CPC ........ *A61B 1/00096* (2013.01); *A61B 1/0011* (2013.01); *A61B 1/00089* (2013.01); *A61B 1/00091* (2013.01); *A61B 1/00101* (2013.01); *A61B 1/00137* (2013.01); *A61B 1/00142* (2013.01); *A61B 1/00177* (2013.01); *A61B 1/00181* (2013.01); *A61B 1/018* (2013.01); *A61B 1/051* (2013.01); *A61B 1/053* (2013.01); *A61B 1/0615* (2013.01); *A61B 1/0676* (2013.01); *A61B 1/0684* (2013.01); *A61B 1/12* (2013.01); *A61B 1/126* (2013.01); *G02B 23/2423* (2013.01); *G02B 23/2461* (2013.01); *G02B 23/2476* (2013.01); *G02B 27/0006* (2013.01)

(58) Field of Classification Search
CPC ............. A61B 1/0008; A61B 1/00096; A61B 1/00101; A61B 1/00177; A61B 1/00174; A61B 1/00179; A61B 1/00183; A61B 1/00676
See application file for complete search history.

(56) References Cited

U.S. PATENT DOCUMENTS

| | | |
|---|---|---|
| 3,889,662 A | 6/1975 | Mitsui |
| 3,918,438 A | 11/1975 | Hayamizu |
| (Continued) | | |

FOREIGN PATENT DOCUMENTS

WO WO 2012/038958 A2 3/2012

*Primary Examiner* — Matthew J Kasztejna
(74) *Attorney, Agent, or Firm* — Bookoff McAndrews, PLLC

(57) ABSTRACT

The present specification describes a circuit board design that uses circuit boards for illuminator sets associated with the various optical assemblies. In one configuration, front and side illuminators are assembled on front and side illuminator circuit boards. Leaf connectors associated with each illuminator are provided to interface with a common base board.

19 Claims, 16 Drawing Sheets

Related U.S. Application Data

15/144,569, filed on May 2, 2016, now Pat. No. 10,070,774, which is a continuation of application No. 14/791,314, filed on Jul. 3, 2015, now Pat. No. 9,351,629, which is a continuation of application No. 13/984,028, filed on Aug. 22, 2013, now Pat. No. 9,101,266.

(60) Provisional application No. 62/352,631, filed on Jun. 21, 2016, provisional application No. 62/286,772, filed on Jan. 25, 2016, provisional application No. 61/439,948, filed on Feb. 7, 2011.

(51) Int. Cl.
    *G02B 23/24*     (2006.01)
    *G02B 27/00*     (2006.01)

(56) References Cited

U.S. PATENT DOCUMENTS

| | | | |
|---|---|---|---|
| 4,292,961 A | 10/1981 | Kawashima | |
| 4,699,463 A | 10/1987 | D'Amelio | |
| 4,868,644 A | 9/1989 | Yabe | |
| 4,971,035 A | 11/1990 | Ito | |
| 5,040,069 A | 8/1991 | Matsumoto | |
| 5,386,817 A | 2/1995 | Jones | |
| 5,411,020 A | 5/1995 | Ito | |
| 5,518,501 A | 5/1996 | Oneda | |
| 5,547,455 A | 8/1996 | McKenna | |
| 5,800,341 A | 9/1998 | McKenna | |
| 5,940,126 A | 8/1999 | Kimura | |
| 6,450,950 B2 | 9/2002 | Irion | |
| 6,605,035 B2 | 8/2003 | Ando | |
| 6,832,984 B2 | 12/2004 | Stelzer | |
| 6,997,871 B2 | 2/2006 | Sonnenschein | |
| 7,108,657 B2 | 9/2006 | Irion | |
| 7,371,209 B2 | 5/2008 | Viebach | |
| 7,553,274 B2 | 6/2009 | Miyake | |
| 7,621,869 B2 | 11/2009 | Ratnakar | |
| 7,775,971 B2 | 8/2010 | Fujimori | |
| 7,967,745 B2 | 6/2011 | Gilad | |
| 8,072,537 B2 | 12/2011 | Schwarz | |
| 8,449,457 B2 | 5/2013 | Aizenfeld | |
| 8,608,648 B2 | 12/2013 | Banik | |
| 8,870,753 B2 | 10/2014 | Boulais | |
| 8,926,502 B2 | 1/2015 | Levy | |
| 9,144,664 B2 | 9/2015 | Jacobsen | |
| 9,402,533 B2 | 8/2016 | Kirma | |
| 9,713,417 B2 | 7/2017 | Levy | |
| 2002/0007110 A1 | 1/2002 | Irion | |
| 2004/0122290 A1 | 6/2004 | Irion | |
| 2004/0158129 A1 | 8/2004 | Okada | |
| 2005/0038317 A1 | 2/2005 | Ratnakar | |
| 2005/0090709 A1 | 4/2005 | Okada | |
| 2005/0119527 A1 | 6/2005 | Banik | |
| 2005/0182299 A1 | 8/2005 | D'Amelio | |
| 2005/0234294 A1 | 10/2005 | Saadat | |
| 2005/0277808 A1 | 12/2005 | Sonnenschein | |
| 2006/0047184 A1 | 3/2006 | Banik | |
| 2006/0183975 A1 | 8/2006 | Saadat | |
| 2006/0252994 A1 | 11/2006 | Ratnakar | |
| 2007/0177008 A1 | 8/2007 | Bayer | |
| 2007/0185384 A1 | 8/2007 | Bayer | |
| 2007/0197875 A1 | 8/2007 | Osaka | |
| 2007/0203396 A1 | 8/2007 | Mccutcheon | |
| 2007/0249907 A1* | 10/2007 | Boulais | A61B 1/05 600/179 |
| 2008/0058601 A1 | 3/2008 | Fujimori | |
| 2008/0167529 A1 | 7/2008 | Otawara | |
| 2008/0275298 A1 | 11/2008 | Ratnakar | |
| 2008/0287961 A1 | 11/2008 | Miyamoto | |
| 2009/0268019 A1 | 10/2009 | Ishii | |
| 2010/0053312 A1 | 3/2010 | Watanabe | |
| 2010/0326703 A1 | 12/2010 | Gilad | |
| 2011/0160530 A1 | 6/2011 | Ratnakar | |
| 2011/0263938 A1 | 10/2011 | Levy | |
| 2012/0053407 A1 | 3/2012 | Levy | |
| 2012/0065468 A1 | 3/2012 | Levy | |
| 2012/0229615 A1 | 9/2012 | Kirma et al. | |
| 2012/0232340 A1 | 9/2012 | Levy et al. | |
| 2012/0232343 A1 | 9/2012 | Levy | |
| 2012/0253121 A1 | 10/2012 | Kitano | |
| 2013/0271588 A1 | 10/2013 | Kirma | |
| 2013/0274551 A1 | 10/2013 | Kirma | |
| 2014/0132804 A1 | 5/2014 | Guissin | |
| 2014/0153916 A1 | 6/2014 | Kintner | |
| 2014/0213850 A1 | 7/2014 | Levy | |
| 2014/0296628 A1 | 10/2014 | Kirma | |
| 2014/0296643 A1 | 10/2014 | Levy | |
| 2014/0296866 A1 | 10/2014 | Salman | |
| 2014/0309495 A1 | 10/2014 | Kirma | |
| 2014/0316198 A1 | 10/2014 | Krivopisk | |
| 2014/0364691 A1 | 12/2014 | Krivopisk | |
| 2015/0358518 A1 | 12/2015 | Ishii | |
| 2017/0215718 A1 | 8/2017 | Schan | |
| 2018/0028053 A1 | 2/2018 | Kirma | |

* cited by examiner

ILLUMINATOR CIRCUIT BOARD ASSEMBLY FOR AN ENDOSCOPE

CROSS-REFERENCE

This application is a continuation of U.S. Nonprovisional patent application Ser. No. 15/610,201, filed on May 31, 2017, which claims the benefit of U.S. Provisional Patent Application No. 62/352,631, filed on Jun. 21, 2016.

U.S. Nonprovisional patent application Ser. No. 15/610,201, filed on May 31, 2017, is a continuation-in-part of U.S. patent application Ser. No. 15/411,103, filed on Jan. 20, 2017, now U.S. Pat. No. 10,517,464, issued Dec. 31, 2019, which relies on U.S. Patent Provisional Application No. 62/286,772, filed on Jan. 25, 2016.

U.S. application Ser. No. 15/411,103 is a continuation-in-part application of U.S. Nonprovisional patent application Ser. No. 15/144,569, filed on May 2, 2016, now U.S. Pat. No. 10,070,774, issued Sep. 11, 2018, which is a continuation of U.S. Nonprovisional patent application Ser. No. 14/791,314, filed on Jul. 3, 2015, now U.S. Pat. No. 9,351,629 issued on May 31, 2016, which is a continuation of U.S. Nonprovisional patent application Ser. No. 13/984,028, filed on Aug. 22, 2013, now U.S. Pat. No. 9,101,266, issued on Aug. 11, 2015, which is a national stage entry application of PCT Application No. PCT/IL2012/050037, filed on Feb. 6, 2012, which claims the benefit of priority of U.S. Provisional Patent Application No. 61/439,948, filed on Feb. 7, 2011. All of the aforementioned applications are herein incorporated by reference in their entirety.

FIELD

The present specification generally relates to an endoscope and specifically relates to an illuminator circuit board assembly for an endoscope.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

Endoscopes, such as colonoscopes, gastroscopes and the like, that are currently being used, typically have a front camera for viewing internal organs, such as the colon, an illuminator, a fluid injector for cleaning the camera lens, and a working channel for inserting surgical tools in order to, for example, remove polyps found in the colon. The illuminators commonly used are fiber optics which transmit light, generated remotely, to the endoscope tip section. The use of light-emitting diodes (LEDs) for illumination is also known. Typically a frame within the endoscope assembly supports one or more illuminators.

While using a scope, during a medical procedure, an illuminator, such as an LED, can turn off due to an internal failure, or due to any other reason such as one or more illuminator components reaching an end of life. Current systems correct such failures mostly by replacing the illuminator. In order to replace an illuminator, a distal tip of the endoscope is required to be opened to replace wires, followed by re-sealing the distal tip. The process of replacing a failed illuminator is cumbersome in terms of time as well as effort required.

There is thus a need for a circuit board that supplies power to each illuminator in the distal tip designed such that it provides easy access to the illuminators, and enables easy replacement of failed illuminator(s) if required. There is also a need for an endoscope tip cover that is more modular and configured to be at least partially opened in a manner that provides direct and easy access to one or more illuminators.

SUMMARY

The following embodiments and aspects thereof are described and illustrated in conjunction with systems, tools and methods, which are meant to be exemplary and illustrative, not limiting in scope.

In some embodiments, the present specification discloses a tip cover for a tip section of a multi-viewing element endoscope, said tip section comprising a front pointing viewing element and at least one side pointing viewing element, wherein each of the front pointing viewing element and at least one side pointing viewing element comprises an image sensor and a lens assembly, said tip cover comprising: a main component portion; a side removable window component located in a side panel recess of said main component portion, said side removable window component further comprising a flat depression which comprises a plurality of windows for accessing optical lens assembly, illuminators and components associated with a side pointing viewing element; and a front panel positioned on a front end of tip cover, said front panel comprising a plurality of windows for accessing optical lens assembly, illuminators and components associated with a front pointing viewing element.

In some embodiments, the present specification discloses a circuit board assembly for use in a tip section of a multi-viewing element endoscope, said tip comprising a front pointing viewing element and at least one side pointing viewing element, wherein each viewing element comprises an image sensor and a lens assembly, said circuit board assembly comprising: a first base board to which the front pointing viewing element is connected; a second base board to which the at least one side pointing viewing element is connected; a third base board to which said first and said second base boards are connected, wherein said first and said second base boards are placed perpendicular to said third base board; and at least one illuminator associated with each of the front and side pointing viewing elements, wherein said circuit board assembly comprises a separate circuit board to hold each illuminator.

Optionally, a first illuminator board to hold a first illuminator set associated with the front pointing viewing element is positioned parallel to the first base board, and comprises an outer side, and an inner side opposite to the outer side and facing the first base board, with said front pointing illuminator set being connected on the outer side.

Optionally, the circuit board assembly further comprises a first electrical pad adapted to interface the front pointing illuminator set to a power source, said first electrical pad being connected to the inner side of the first illuminator board.

Optionally, at least one second illuminator board to hold at least one second illuminator set associated with at least one side pointing viewing element is positioned parallel to the second base board, and comprises an outer side, and an inner side opposite to the outer side and facing the second base board, with said side pointing illuminator set being connected on the outer side.

Optionally, the circuit board assembly further comprises a second electrical pad adapted to interface the side pointing illuminator set to a power source, said second electrical pad being connected to the inner side of the second illuminator board.

Optionally, the circuit board assembly further comprises at least one first connector having a first end attached to the third base board and a second end adapted to contact the first electrical pad, wherein the second end is opposite to said first end, said at least one first connector facing the inner side of the first illuminator board; and at least one second connector having a first end attached to the third base board and a second end adapted to contact the second electrical pad, wherein the second end is opposite to the first end, said at least one second connector facing the inner side of the second illuminator board.

Optionally, the at least one first connector and the at least one second connector are leaf connectors.

Optionally, the second end of the at least one first connector and the at least one second connector has a square shape.

Optionally, the second end of the at least one first connector and the at least one second connector has a rectangular shape.

Optionally, the second end of the at least one first connector and the at least one second connector has a circular shape.

Optionally, the at least one first connector and the at least one second connector are spring connectors.

Optionally, at least one of the first electrical pad and the second electrical pad is a printed circuit board.

Optionally, the first and the second base boards are placed perpendicular to each other.

Optionally, said first illuminator board is shaped as a "U" and is configured to hold three illuminators associated with the front pointing viewing element.

Optionally, said at least one second illuminator board is shaped as a "U" and is configured to hold two illuminators associated with the at least one side pointing viewing element.

Optionally, the circuit board assembly comprises two side illuminator boards parallel to the second base board, wherein each side illuminator board is positioned on either side of the second base board, to hold illuminator sets for two side viewing elements on opposing sides.

Optionally, each of the said side illuminator circuit boards is shaped as a "U" and is configured to hold two illuminators associated with a side pointing viewing element.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein.

DETAILED DESCRIPTION

In an embodiment, the present specification discloses a circuit board design for the tip of an endoscope system. The circuit board design not only makes more efficient use of the space inside the distal tip, which is crowded with components, but also reduces the cost of the assembly and makes the design easier to scale compared to existing circuit board designs for multiple viewing element endoscopes. In one embodiment, leaf connectors are used to interface illuminator sets associated with various optical assemblies. In one embodiment, illuminator sets are placed on independent illuminator circuit boards connected to a common base board, enabling them to draw power through the leaf connectors from a main power source. This allows the illuminator circuits to draw power without using any wires.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

Figure 1:
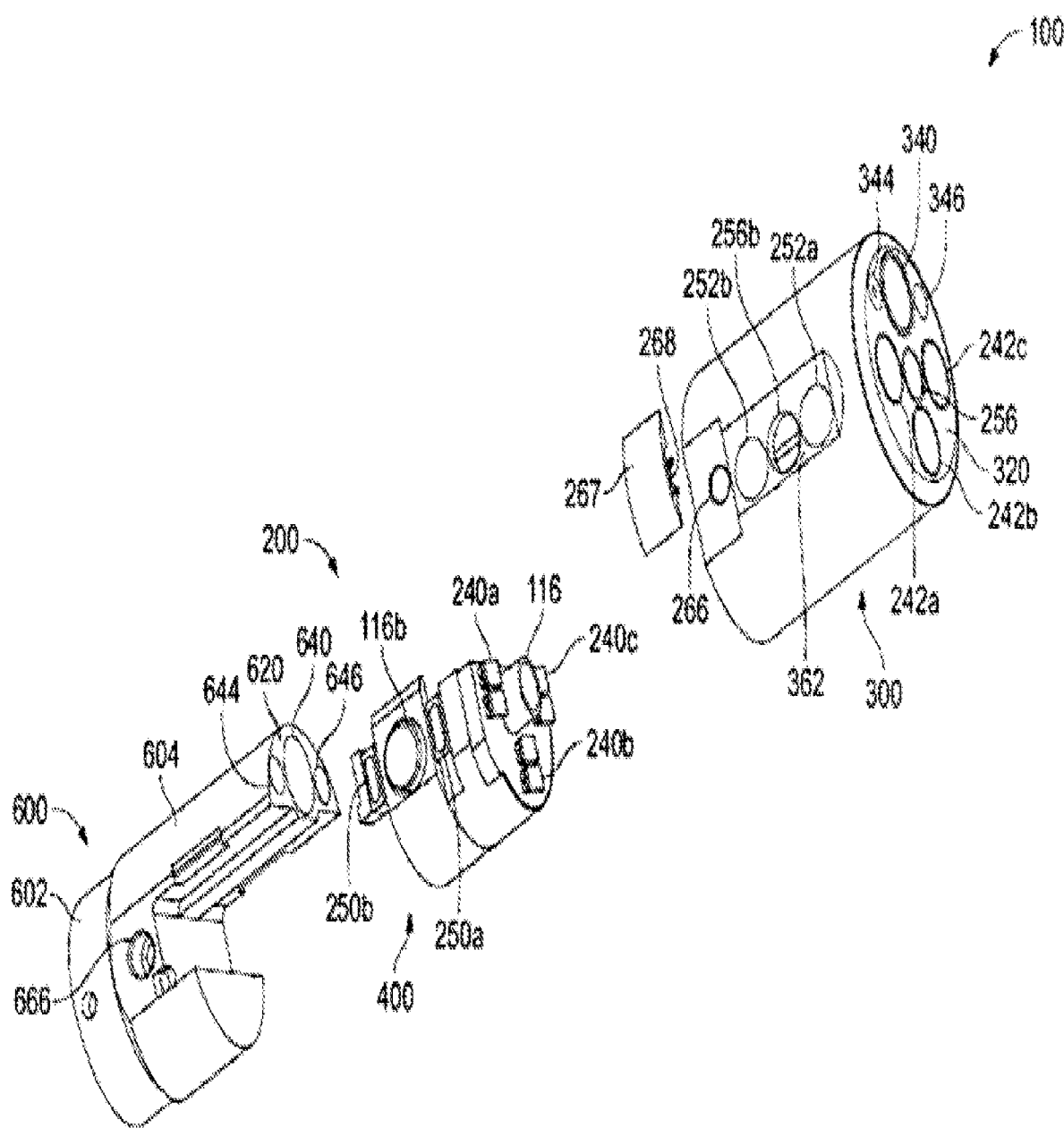
FIG. 1 illustrates an exploded view of a tip section of an endoscope assembly according to one embodiment of the present specification.

Reference is now made to FIG. 1, which shows an exploded view of a tip section 200 of a multi-viewing element endoscope assembly 100 comprising at least one front working/service channel, according to various embodiments. It is noted that the term "endoscope" as mentioned to herein may refer particularly to a colonoscope or gastroscope, according to some embodiments, but is not limited only to colonoscopes and gastroscopes. The term "endoscope" may refer to any instrument used to examine the interior of a hollow organ or cavity of the body.

According to an embodiment, tip section 200 of endoscope 100 includes a tip cover 300, an electronic circuit board assembly 400 and a fluid channeling component 600.

According to some embodiments, fluid channeling component 600 may be configured as a separate component from electronic circuit board assembly 400. This configuration may be adapted to separate the fluid channels, and at least one front working/service channel, such as working/service channel 640, which are located in fluid channeling component 600, from the sensitive electronic and optical parts which may be located in the area of electronic circuit board assembly 400. Thus, the component structure of the tip section 200 enables effective insulation of the plurality of electronic elements from the plurality of fluid channels.

Tip section 200 may be turnable by way of flexible shaft which is also referred to as a bending section, for example a vertebra mechanism.

In some embodiments, electronic circuit board assembly 400 is configured to carry a front viewing element 116 and at least one side viewing element 116*b*, which may include a sensor such as but not limited to a Charge Coupled Device (CCD) or a Complementary Metal Oxide Semiconductor (CMOS) image sensor. In addition, electronic circuit board assembly 400 may be configured to carry a second side viewing element (not shown) on the opposite side of side viewing element 116*b*, which may include a sensor such as but not limited to a Charge Coupled Device (CCD) or a Complementary Metal Oxide Semiconductor (CMOS) image sensor. Side viewing elements may or may not be similar to front viewing element 116.

Electronic circuit board assembly 400 may further be configured to carry front illuminator sets 240*a*, 240*b*, 240*c*, which are, in one embodiment, associated with front viewing element 116 and are positioned to illuminate the fields of view of front viewing element 116.

In addition, electronic circuit board assembly 400 may further be configured to carry side illuminator sets 250*a* and 250*b*, which are, in one embodiment, associated with side viewing element 116*b* and are positioned to essentially illuminate the fields of view of side viewing element 116*b*. Electronic circuit board assembly 400 may also be configured to carry side illuminator sets, which are associated with a second side viewing element that is positioned on the opposite side of side viewing element 116*b*, which may be similar to side illuminators 250*a* and 250*b*.

Front illuminator sets 240*a*, 240*b*, 240*c* and side illuminator sets 250*a* and 250*b* may optionally be discrete illuminators and may include a light-emitting diode (LED), which may be a white light LED, an infrared light LED, a near infrared light LED, an ultraviolet light LED or any other LED.

Each of the front illuminator sets 240*a*, 240*b*, 240*c* and side illuminator sets 250*a* and 250*b* may include one, two, three or more LEDs.

The term "discrete", concerning discrete illuminator, may refer to an illumination source, which generates light internally—in contrast to a non-discrete illuminator, which may be, for example, a fiber optic merely transmitting light generated remotely.

Figure 2A:
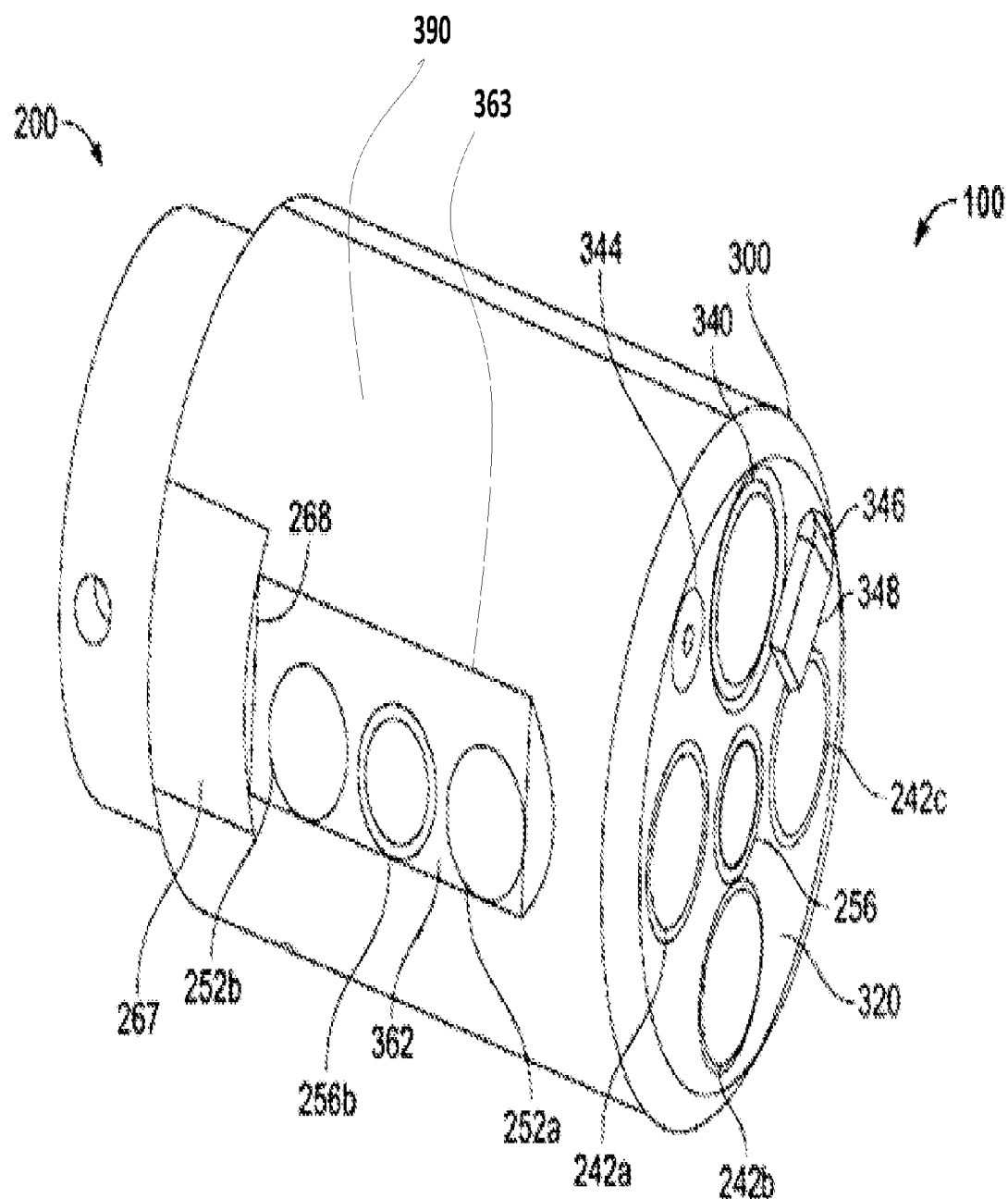
FIG. 2A illustrates a perspective view of a tip section of an endoscope assembly according to one embodiment of the present specification.
Figure 2B:
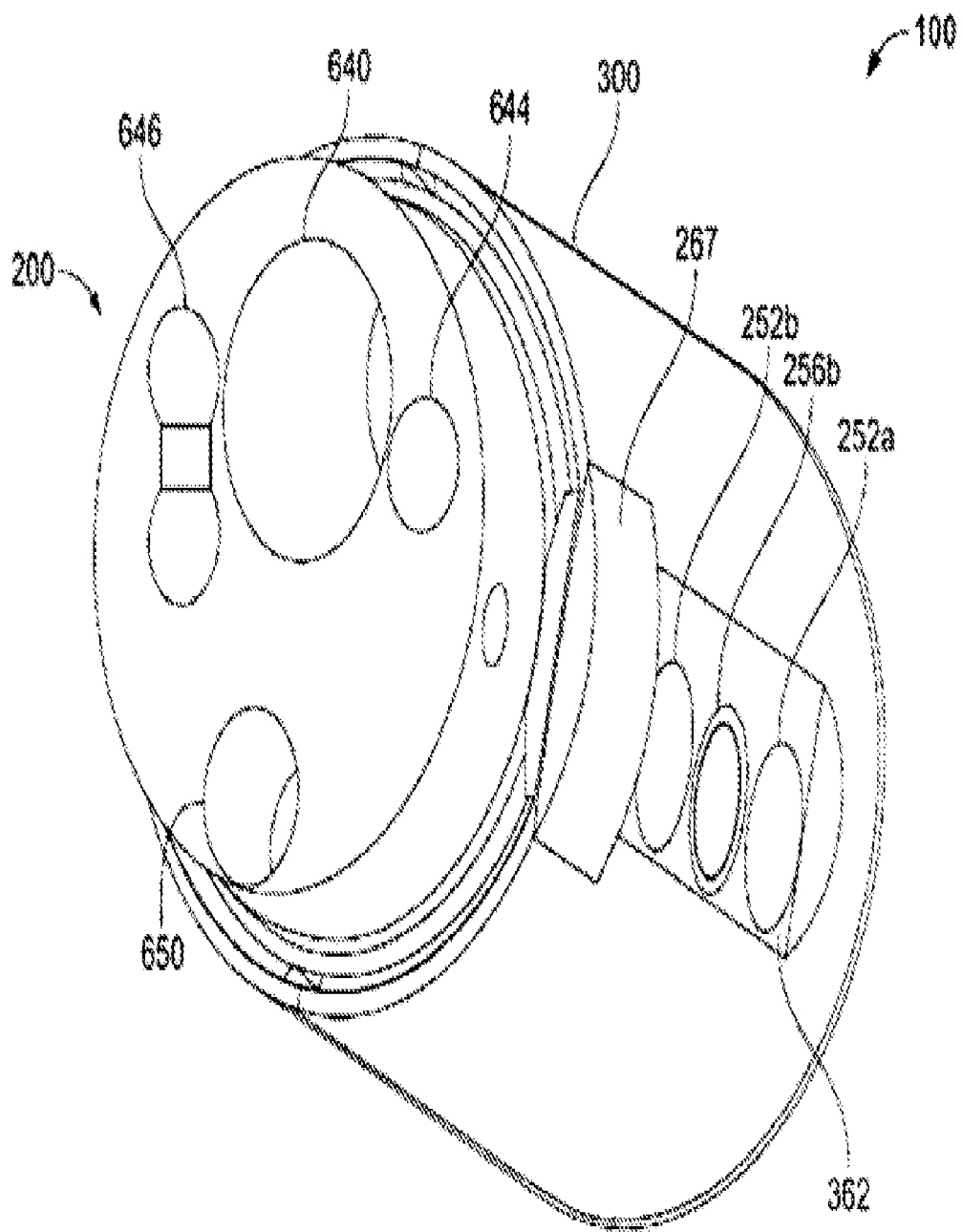
FIG. 2B illustrates another perspective view of a tip section of an endoscope assembly according to one embodiment of the present specification.

Reference is now made to FIG. 1 along with FIG. 2A and FIG. 2B, which show a perspective view of a tip section 200 of an endoscope assembly 100 according to an embodiment.

Tip cover 300 may be configured to fit over the inner parts of tip section 200 including electronic circuit board assembly 400 and fluid channeling component 600 and to provide protection to the internal components in the inner parts.

Tip cover 300 may include a front panel 320 having a transparent surface, window, or opening for front optical lens assembly 256, of front looking camera or viewing element 116. Front optical lens assembly 256 may include a plurality of lenses, static or movable, which may provide a field of view of 90 degrees or more, 120 degrees or more, or up to essentially 180 degrees. Front optical lens assembly 256 may provide a depth of field in the range of about 3 to 100 millimeters.

The term depth of field or focal length may be used to refer to the distance from a lens to a sensor or may be used to refer to the distance, from the lens, over which an object remains in focus. One of ordinary skill in the art would understand what definition for depth of field is being used based on the context and distances discussed.

An optical axis of front looking camera or viewing element 116 may be essentially directed along the long dimension of the endoscope. However, since front viewing element 116 is typically a wide angle viewing element, its field of view may include viewing directions at large angles to its optical axis. Additionally, front panel 320 may include optical windows 242a, 242b and 242c of illuminators 240a, 240b and 240c, respectively. It should be noted that the number of illumination sources used for illumination of the field of view may vary.

In addition, front panel 320 may include a working channel opening 340 of a working channel 640. In alternate embodiments, the front panel may include more than one working channel opening.

Jet channel opening 344 of jet channel 644 may also be located on front panel 320 of tip cover 300. Jet channel 644 may be configured for providing high-pressure jet of fluid such as water or saline for cleaning the walls of the body cavity.

Also located on front panel 320 of tip cover 300 is injector opening 346 of injector channel 646, having a nozzle (not shown) aimed at front optical lens assembly 256. Injector channel 646 may be configured for injecting fluid (liquid and/or gas) to wash contaminants such as blood, feces and other debris from a surface of the front optical lens assembly 256 of the front viewing element 116. Optionally, injector channel 646 may be configured for cleaning front optical lens assembly 256 and one, two, or all of optical windows 242a, 242b and 242c. Injector channel 646 may be fed by fluid such as water and/or gas which may be used for cleaning and/or inflating a body cavity.

Visible on the sidewall 362 of tip cover 300 is side optical lens assembly 256b for side viewing element 116b, which may be similar to front optical lens assembly 256 and optical windows 252a and 252b of illuminators 250a and 250b for side viewing element 116b. Also on the sidewall 362 of tip cover 300, on the opposing side of first side optical lens assembly 256b, is a second optical lens assembly for a second side viewing element, which may be similar to side optical lens assembly 256b and optical windows 252a and 252b of illuminators 250a and 250b for side viewing element 116b. In one embodiment, the first side optical lens assembly 256b may provide a depth of field in the range of about 3 to 100 millimeters.

An optical axis of the first side viewing element 116b may be essentially directed perpendicular to the long dimension of the endoscope. An optical axis of the second side viewing element may be essentially directed perpendicular to the long dimension of the endoscope. However, since each side viewing element typically comprises a wide angle camera, its field of view may include viewing directions at large angles to its optical axis. In accordance with some embodiments, each side viewing element has a field of view of 90 degrees or more, 120 degrees or more, or up to essentially 180 degrees.

In addition, side injector opening 266 of side injector channel 666 may be located at distal end of sidewall 362. A nozzle cover 267 may be configured to fit side injector opening 266.

Additionally, nozzle cover 267 may include a nozzle 268 which may be aimed at side optical lens assembly 256b and configured for injecting fluid to wash contaminants such as blood, feces and other debris from a surface of side optical assembly 256b of side viewing element 116b. The fluid may include gas which may be used for inflating a body cavity. Optionally, nozzle 268 may be configured for cleaning both side optical lens assembly 256b and optical windows 252a and/or 252b.

According to some embodiments, side injector channel 666 may be configured to supply fluids for cleaning any of the tip elements (such as any optical assembly, optical lens assembly, windows, illuminators, and other elements).

Optionally, injector channel 646 and side injector channel 666 may be fed from the same channel.

It is noted that according to some embodiments, although tip section 200 is presented herein showing one side thereof, the opposing side may include elements similar to the side elements described herein (for example, side viewing element, side optical lens assembly, injector(s), nozzle(s), illuminator(s), window(s), opening(s) and other elements).

Sidewall 362 may have a form of an essentially flat surface which assists in directing the cleaning fluid injected from injector channel 666 towards side optical lens assembly 256b and optical windows 252a and/or 252b. Lack of such flat surface may result in dripping of the cleaning fluid along the curved surface of tip section 200 of the endoscope without performing the desired cleaning action.

In accordance with an embodiment, the sidewall 362 is located in a notch/depression in the tip cover 300. This way, side injector opening 266 and corresponding side nozzle 268 may be elevated from the depressed sidewall 362 but still not significantly protrude from the level of cylindrical surface of the tip cover 300. According to an aspect of one embodiment, as shown in FIG. 2A, the sidewall 362 is located in a sufficiently well-defined or deep notch/depression 363 in the tip cover 300 such that the lens assembly of side optical lens assembly 256b stays sufficiently embedded in the notch/depression 363 and well below the level 390 of the cylindrical surface of the tip cover 300. The notch/depression 363 protects the sidewall 362 and components thereof (side optical lens assembly 256b, side illuminators 250a, 250b and side nozzle 268) from both longitudinal and latitudinal mechanical shocks.

It is noted that according to some embodiments, tip section 200 may include more than one side looking camera. In this case, the side looking cameras may be installed such that their fields of view are substantially opposing. However, different configurations and number of side looking cameras are possible within the general scope of the current specification.

Figure 3A:
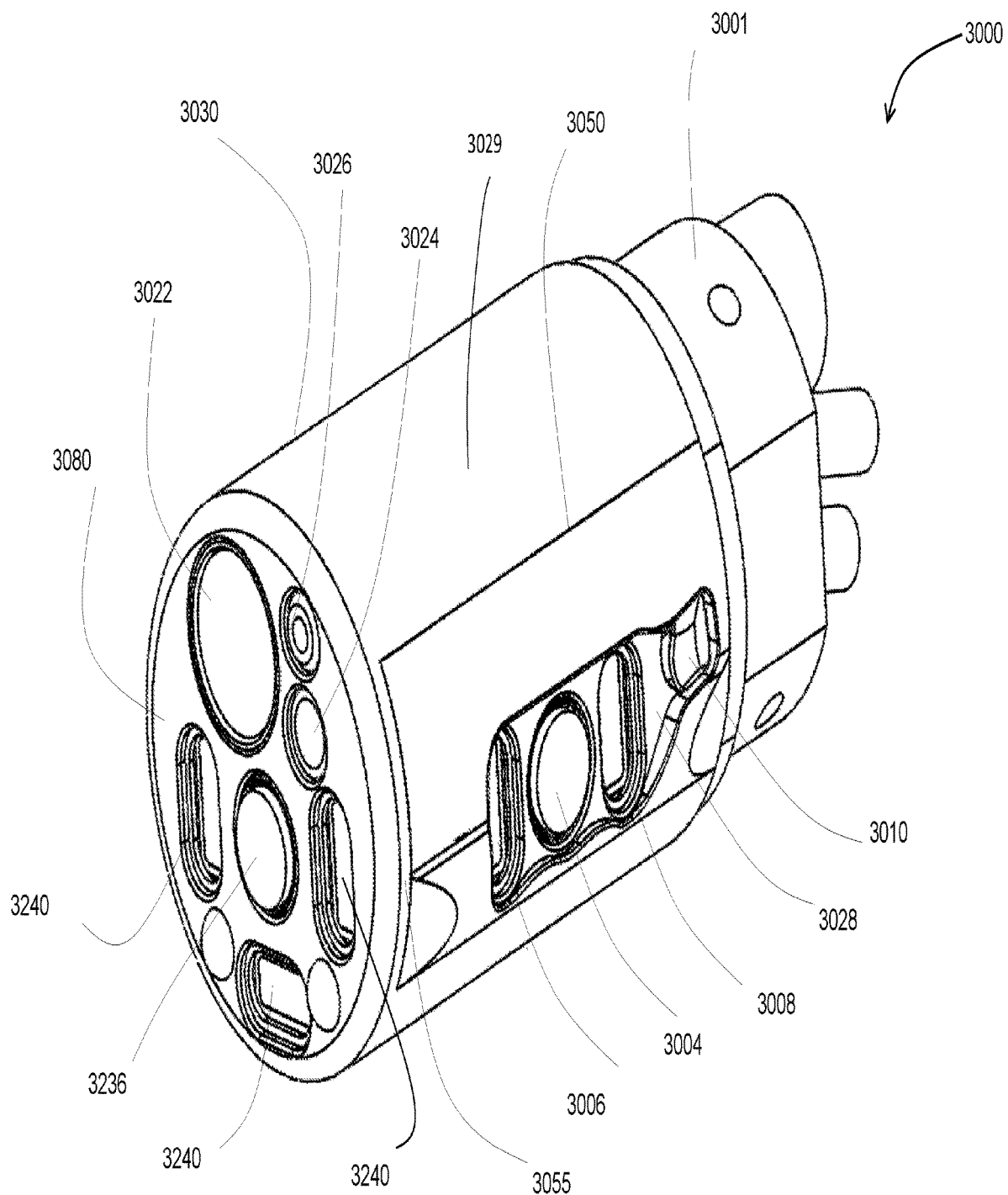
FIG. 3A is an isometric view of one embodiment of a multi-element tip cover positioned over the inner parts of a tip section of a multiple viewing elements endoscope.

FIG. 3A shows an isometric view of another embodiment of a multi-element tip cover 3000. Referring to FIG. 3A, multi-element tip cover 3000 has a main component portion 3030 and a side removable window component 3050 located in a side panel recess or opening 3055 of main component portion 3030. Side removable window component 3050 is sized and configured to fit within a side panel opening or recess 3055. Main component portion 3030 is configured to cover a major portion of a tip section 3001 of an endoscope. Side removable window component 3050 in one embodiment is in the form of a removable panel. In one embodiment, side removable window component 3050 comprises a flat depression 3028 which comprises a window or opening 3004 for a side optical lens assembly, optical windows 3006, 3008 for illuminators, and a side nozzle 3010 opening for a side nozzle.

A front panel 3080 is positioned on a front end of tip cover 3000. Front panel 3080 comprises a window or opening 3236 to a front optical lens assembly, optical windows 3240 for front illuminators, a working/service channel opening 3022, a nozzle opening 3024 and a jet opening 3026.

It may be noted that the overall shape of the distal tip is substantially round, yet the side components including the side camera, LEDs, and jet are placed in a flat, planar depression 3028. This flat, planar depression 3028 is located on a surface of side removable window component 3050.

In one embodiment, multi-element tip cover 3000 has one side removable window component 3050 on one side. In another embodiment, multi-element tip cover 3000 has more than one side removable window component on its tip side surfaces to enable easy access to the internal components in the tip section, such that a component may be removed or replaced if required without having to remove the entire tip cover 3000.

Figure 3B:
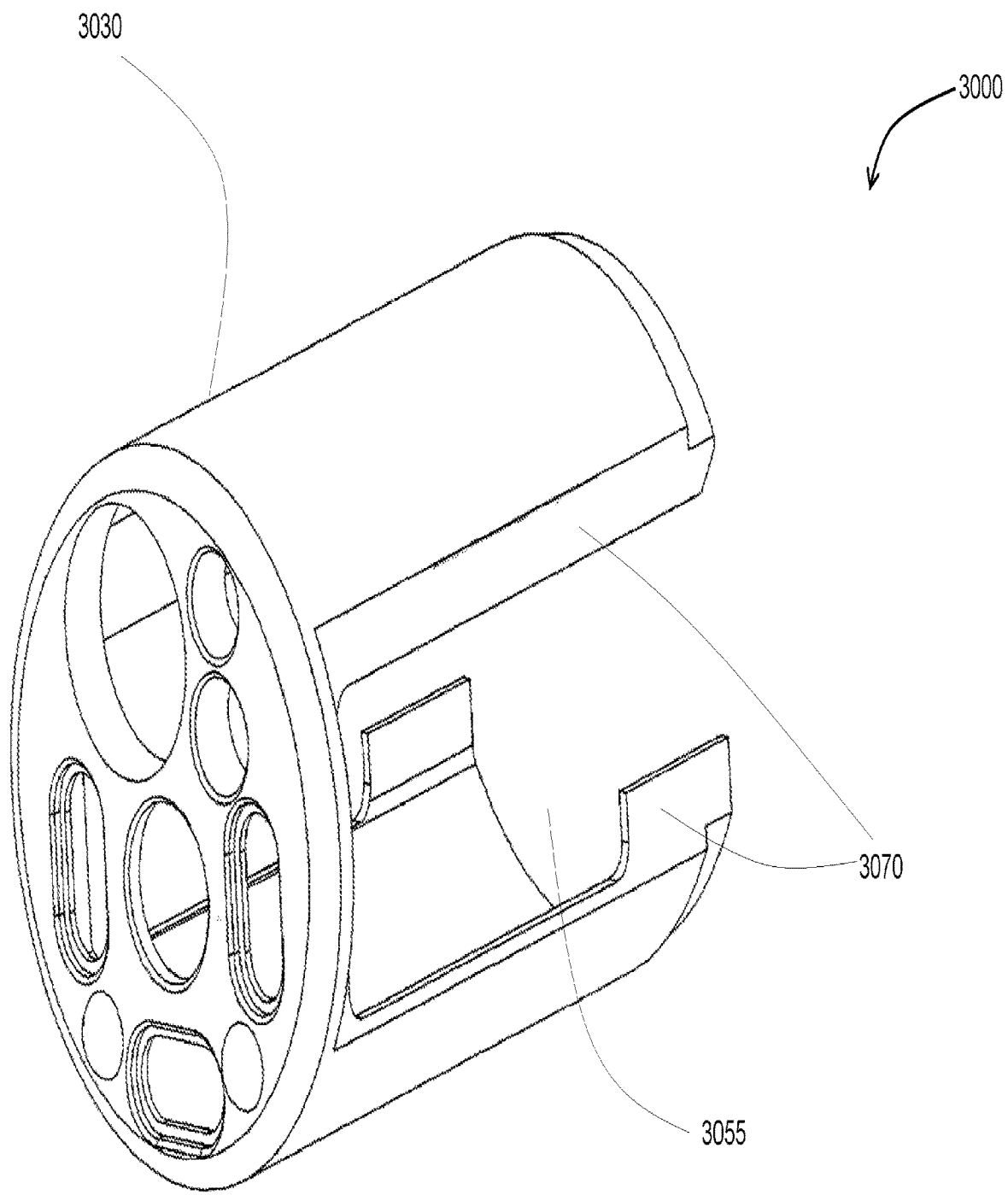
FIG. 3B is an isometric view of a main component portion of the multi-element tip cover of FIG. 3A.

FIG. 3B shows another isometric view of multi-element tip cover 3000 of FIG. 3A. In this figure, side removable window component (shown as side removable window component 3050 in FIG. 3A) is removed, exposing side panel opening or recess 3055. In one embodiment, side panel opening or recess 3055 is positioned on the circumference of the endoscope tip at a distance (depth) ranging from approximately 1 to 9 millimeters from the surface of the tip, and in an embodiment is positioned at approximately 7.0 or 7.9 millimeters, from the surface of the tip.

In one embodiment, main component portion 3030 comprises edges 3070 about side panel opening or recess 3055 that are adapted to couple to the side removable window component, in a manner such that the side removable window component may easily be put on to cover side panel opening or recess 3055 and may also be easily removed. In an embodiment, the side removable window component may be coupled to edges 3070 of the main component portion 3030 by any suitable coupling means known in the art, such as but not limited to screws, hinges, hooks, adhesives or welding. Optionally, in some embodiments, wherein an endoscope includes side viewing elements on both sides of a tip section, tip cover 3000 includes another side panel opening or recess (not shown) positioned on the opposite side of the side panel opening or recess 3055 and another side removable window component for that side panel opening or recess.

Figure 3C:
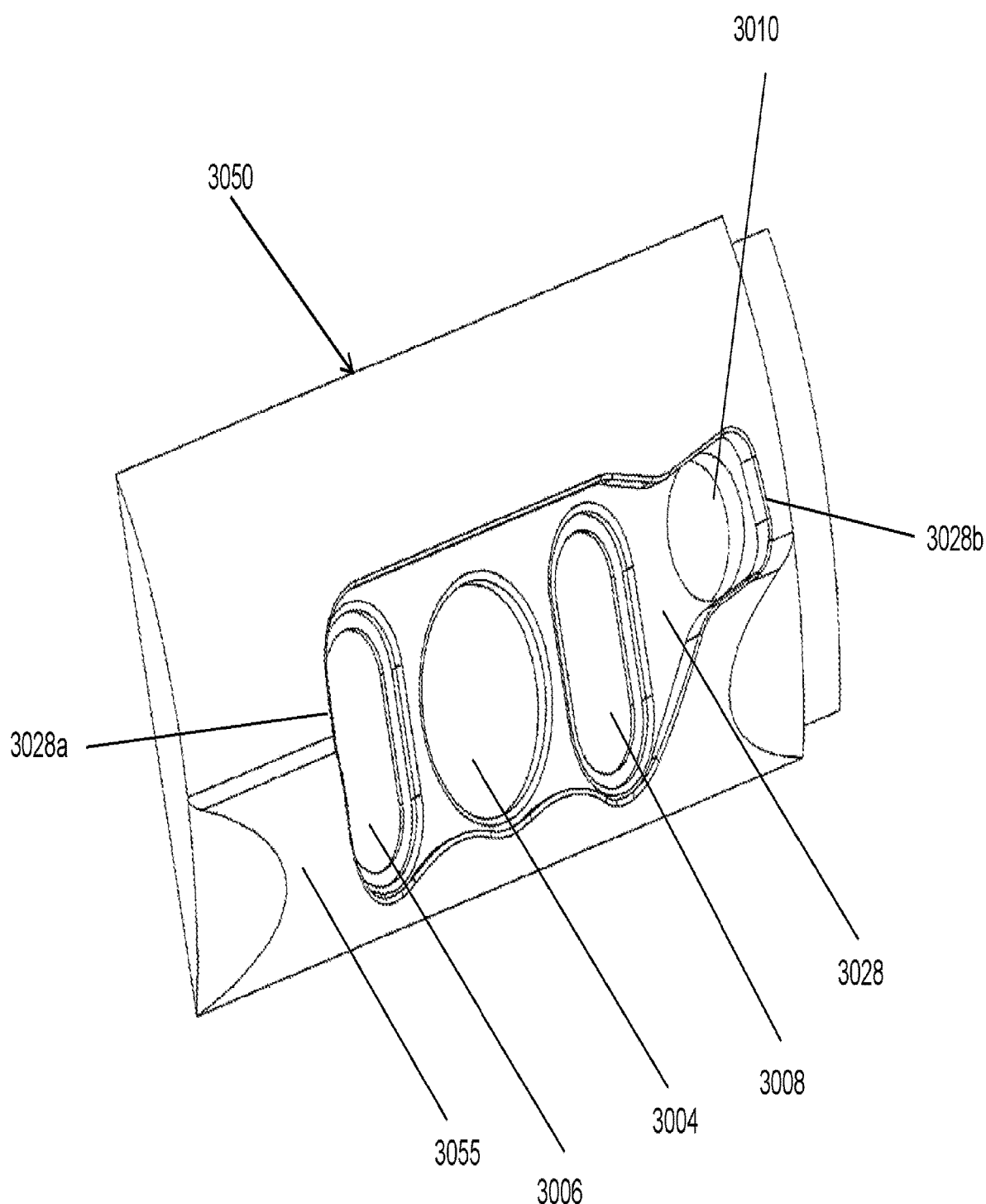
FIG. 3C is an isometric view of a removable window component of the multi-element tip cover of FIG. 3A, according to one embodiment.

FIG. 3C shows the side removable window component 3050 for multi-element tip cover 3000 of FIG. 3A. In an embodiment, side removable window component 3050 is substantially curved along its long axis, and is configured to cover a side portion of a tip section of an endoscope. In one embodiment, a flat depression 3028 is located in a surface 3051 of the side removable window component 3050. A window or opening 3004 for a side optical lens assembly, optical windows 3006, 3008 for illuminators, and side nozzle opening 3010, are placed in the flat depression 3028. In one embodiment, the outline of the flat depression area 3028 is designed such that it conforms to the size and shape of the windows ingrained in it, the windows themselves being designed in accordance with the shape and size of the components they provide access to, and yet occupies a minimal amount of space on the side removable window component. In one embodiment, the flat depression 3028 is wider on one end 3028a to accommodate windows for side optical lens assembly and the illuminators, and narrow at the other end 3028b to conform to the small size of nozzle opening 3010. In various embodiments, the side removable window component 3050 comprises a surface area in a range of 30 to 85% of the total surface area of the cylindrical side wall 3029 of the tip cover 3000 and, in turn, the flat depression 3028 comprises a surface area in a range of 0.50 to 90% of the total surface area of the side removable component 3050 In various embodiments, an aspect ratio of width to length of the side removable window component 3050 is in a range of 1:6 and an aspect ratio of width to length of the flat depression 3028 is in a range of 1:10. In various embodiments, when the side removable window component 3050 is in place on said main component 3030, a distance from the windows 3004, 3006, 3008 of the removable window component 3050 to the underlying optical elements and/or LEDs is in a range of 0 to 3 millimeters, and any increment therein.

Figure 4:
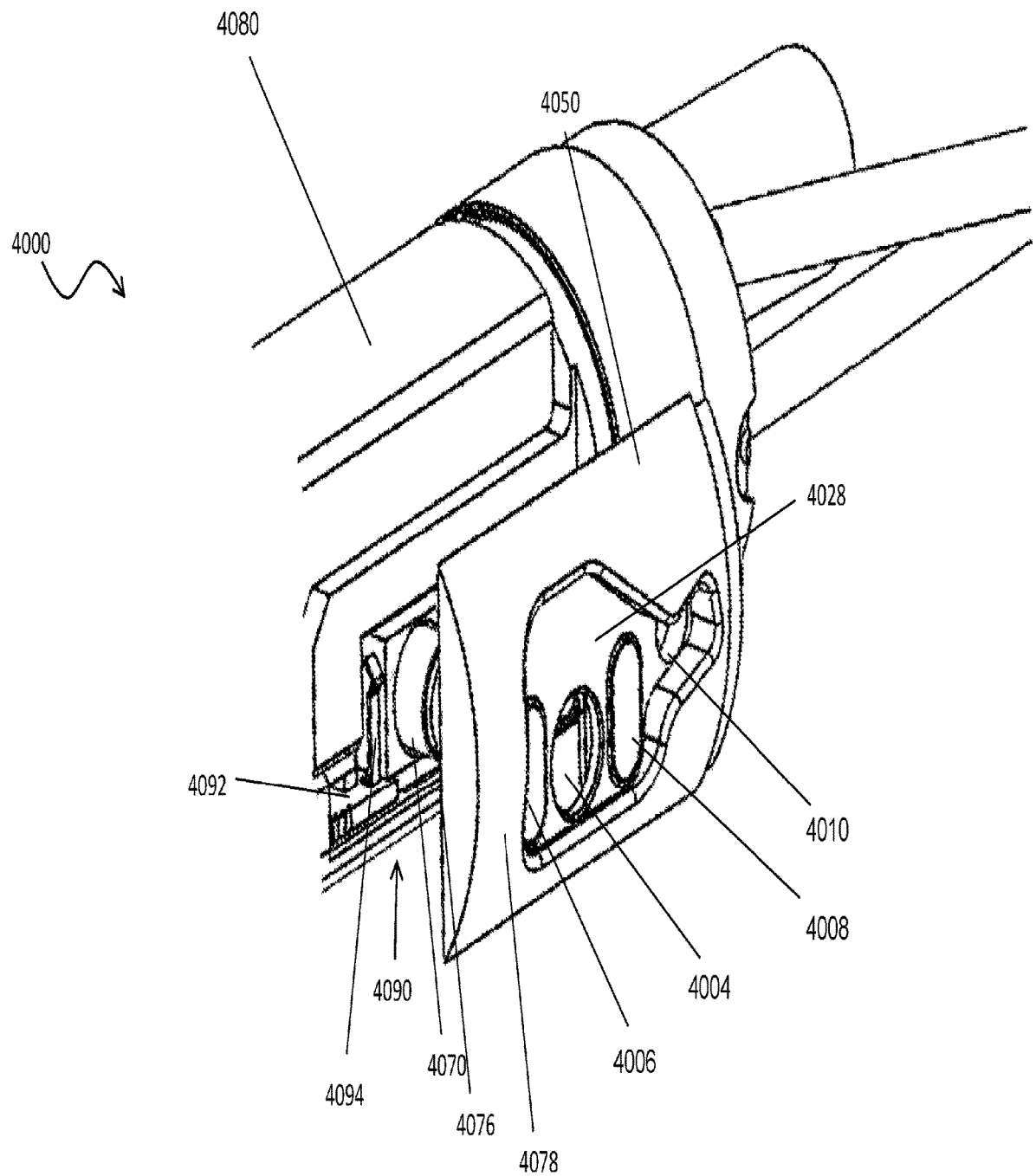
FIG. 4 illustrates a view of a multi-element tip with a side removable window component located in a side panel recess or opening of a main component portion of the multi-element tip cover of FIG. 3A, in accordance with an embodiment.

FIG. 4 illustrates a view of a multi-element tip 4000 with a side removable window component 4050 located in a side panel recess or opening of a main component portion of the multi-element to cover (not shown). Side removable window component 4050, and other related components, may be similar to side removable window component 3050 described in context of FIGS. 3A-3C. Side removable window component 4050 in one embodiment is in the form of a removable panel. In one embodiment, side removable window component 4050 comprises a flat depression 4028 which comprises a window or opening 4004 for a side optical lens assembly 4070, windows 4006, 4008 for illuminators, and a side nozzle 4010. In embodiments, the numbers of windows for illuminators varies with variation in the number of illuminator sets. Preferably side removable component 4050 comprises a substantially planar surface 4076 that attaches to the side of the endoscope tip and a domed surface 4078 extending outward from the substantially planar surface. The domed surface 4078, which forms the curved external surface of the endoscope tip, has embedded therein a depression 4028 within which the openings or windows 4004 for a side optical lens assembly 4070, illuminators 4006, 4008, and a side nozzle 4010 are positioned. Each of the openings or windows 4004 are positioned to align with its corresponding underlying electronic or physical component such that the side optical lens window aligns with the side optical lens, the illuminator windows align with the illuminators, and the side nozzle opening aligns with the side nozzle.

FIG. 4 also illustrates position of side removable window component 4050 in proximity to a fluid channeling component 4080 and an electronic component 4090. A main base board assembly (electronic circuit board) 4092 of electronics component 4090 is associated with fluid channeling component 4080, and is adapted to support the front (not shown) and at least one side optical assembly 4070, and the illuminators associated with the at least one side optical assembly 4070. In embodiments, electronics component 4090 is a part of the endoscope and houses sensors, such as but not limited to a CCD or a CMOS sensor, and related components. In one embodiment, leaf connectors are perpendicularly placed on electronic circuit board 4092 surrounding the viewing elements. The figure shows one such leaf connector 4094, which in an embodiment, is placed around side optical assembly 4070. In embodiments, leaf connectors introduce an interface, for the illuminators, to a power source. In most cases, the power source is controlled through a main control box connected to the endoscope. In some embodiments, a leaf connector is a spring-based connector in which a member is spring-loaded against another member to provide a compressive force, thereby holding a component in place, and preferably is metallic so as to also provide an electric connection.

Figure 5:
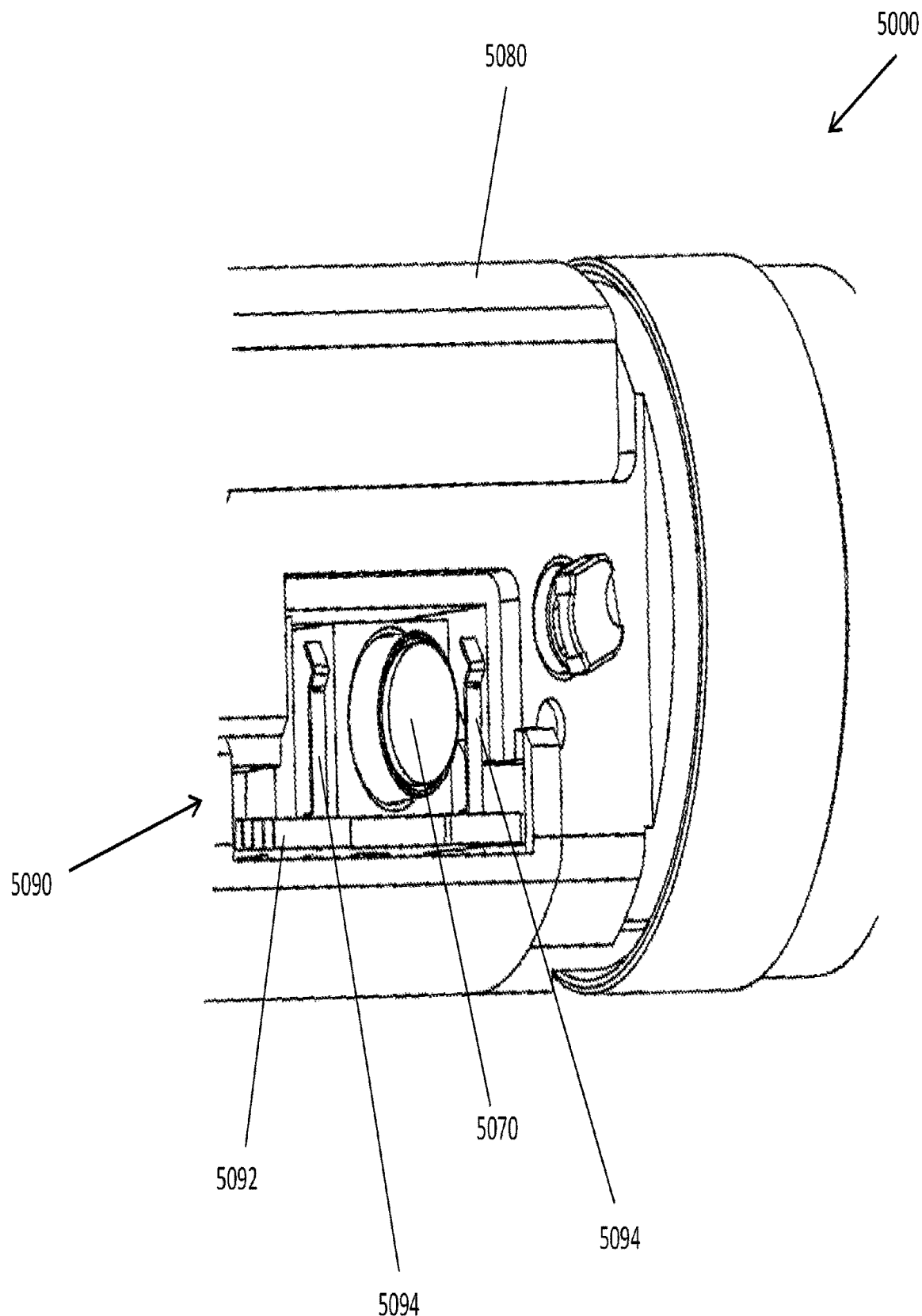
FIG. 5 illustrates another view of an endoscope's tip, having a fluid channeling component and an electronics component, in accordance with an embodiment.

FIG. 5 illustrates another view of an endoscope tip 5000, having a fluid channeling component 5080 and an electronics component 5090. In the figure, side removable window component (as seen in FIGS. 3A, 3C, and 4) is not shown, thereby revealing the components that fit within the depression of the side removable window component. In embodiments, leaf connectors 5094 are adapted to reversibly connect an illuminator electronic circuit board to a main base board assembly (electronic circuit board) 5092 of scope tip 5000. Leaf connectors 5094 enable the illuminator to connect to an electricity source. In embodiments, leaf connectors similar to connectors 5094 are provided along with front illuminators (not shown) and a second set of side illuminators (not shown) of endoscope tip 5000. In embodiments, different types of illuminators (not shown) may comprise LEDs (Light Emitting Diode) adapted to emit white light, infrared light, ultraviolet light, near-infrared light and other wavelengths of light and each type of illuminator may have a different size. In some embodiments, leaf connectors 5094 vary in shape and size with the variation in the type of corresponding illuminators. It should be noted herein that the location and size of the leaf connectors may also be dependent on the relative positions of the individual components within electronics component 5090 and, in particular, the position of the image sensor (s), since adequate light must be available to the sensor to produce a good image.

Figure 6A:
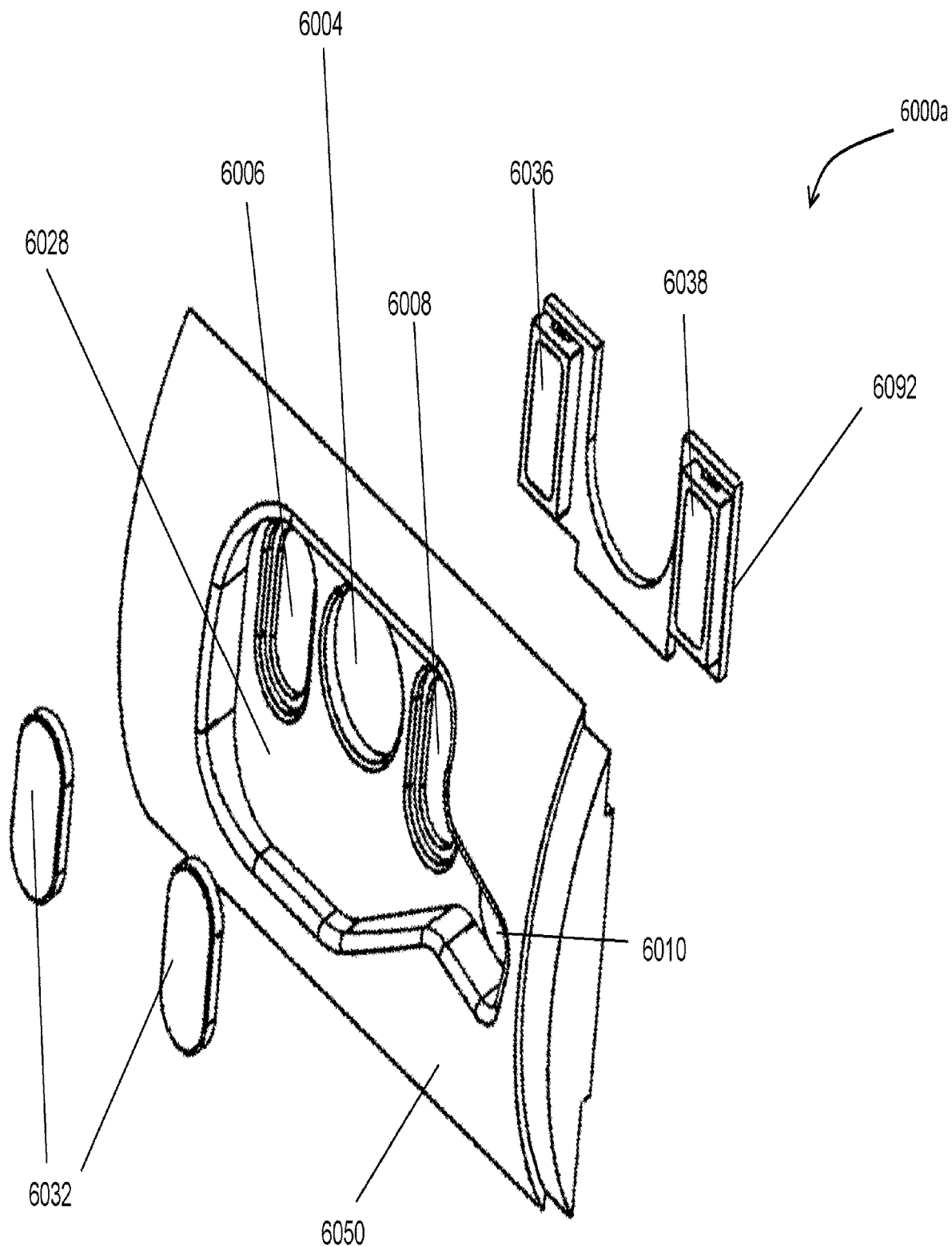
FIG. 6A is a front view of a side removable panel (removable window component) of a multi-element tip cover's outer side, in accordance with an embodiment of the present specification.

FIG. 6A illustrates an exemplary front view 6000a of a side removable panel (removable window component) 6050 of a multi-element tip cover's outer side, in accordance with an embodiment of the present specification. Panel 6050 includes several components such as a side viewing element opening 6004, side illuminators openings 6006 and 6008, and a nozzle opening 6010, located within a flat depression 6028, similar to the components of FIGS. 3C and 4. Additionally, FIG. 6 illustrates outer windows 6032 that may be placed above openings 6006 and 6008. Windows 6032 may be transparent or translucent windows that protect sets of illuminators 6036 and 6038 that respectively illuminate through openings 6006 and 6008. In embodiments, windows 6032 are glass windows that cover the illuminators and seal illuminators openings 6006 and 6008. Sealing prevents damage to the internal electronic components during reprocessing of the endoscope unit. Each set of illuminators 6036 and 6038 may include one, two, three, or more illuminators. Windows 6032 may also enable optimal distribution of light emitted by illuminator sets 6036 and 6038. In embodiments, side illuminator sets 6036 and 6038 are placed over a side illuminators electronic board 6092, which may be similar to board 5092 described in context of FIG. 5. In embodiments, board 6092 is connected to a base board (not shown) of the endoscope. Side illuminators electronic board 6092 may be adapted to carry at least one set of illuminators arranged on both side of the viewing element in order to provide optimal illumination to the viewing element assembly. In one embodiment, board 6092 is shaped as a 'U' and holds side illuminator sets 6036 and 6038 in place. In various embodiments, the length of side illuminator electronic circuit board 6092 ranges from 7.5 mm to 9.5. In various embodiments, the height of side illuminator electronic circuit board 6092 ranges from 3.0 mm to 5.5 mm.

In one embodiment, the circuit board assembly of the present specification can also be adapted for use with CCD sensors. That is, the same circuit board is designed as a common platform that can support either of the two technologies, CCD or CMOS, depending upon the application and requirement.

Figure 6B:
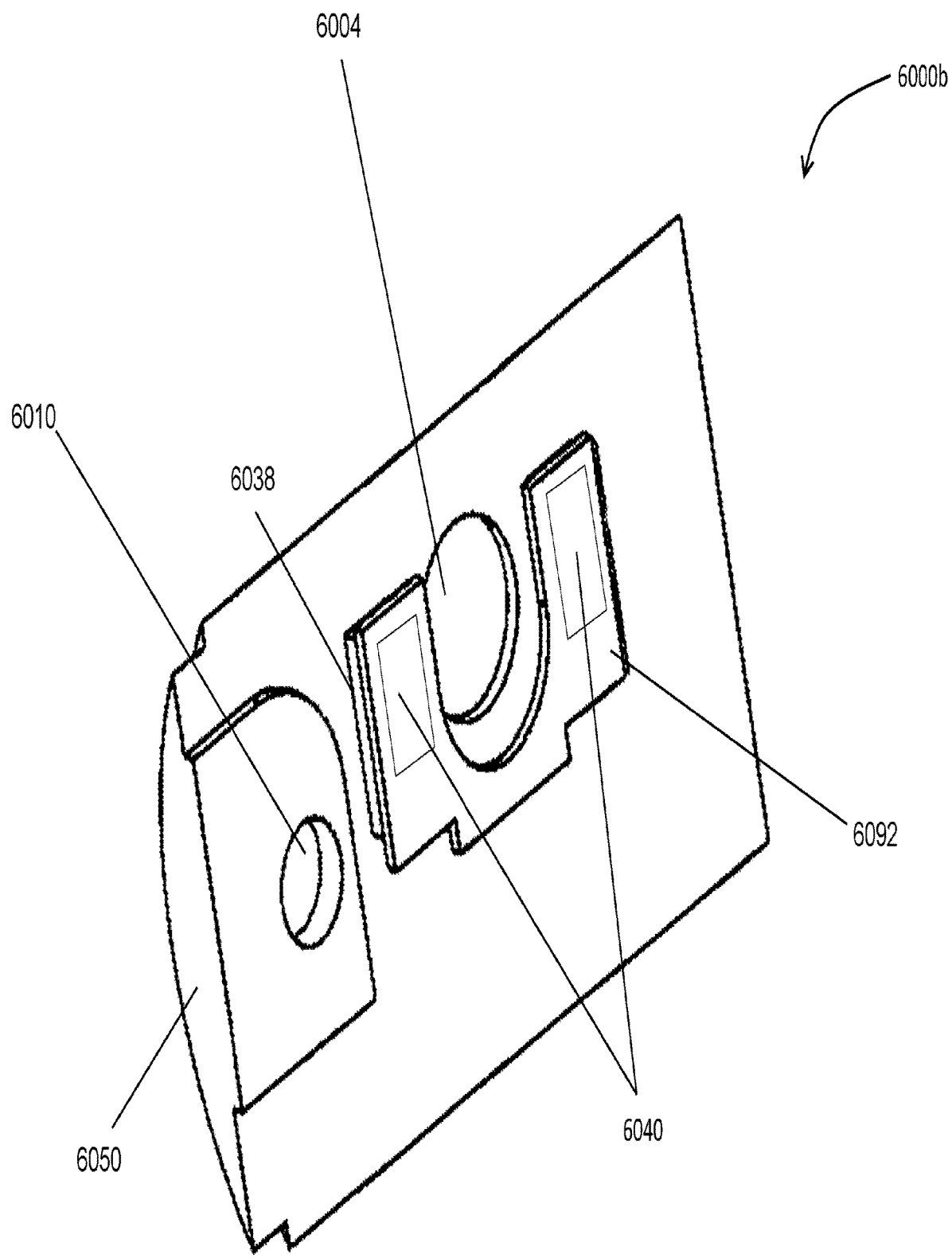
FIG. 6B is a rear view of a side removable panel (removable window component) shown in FIG. 6A, in accordance with an embodiment of the present specification.

FIG. 6B illustrates an exemplary rear view 6000b of side removable panel (removable window component) 6050 shown in FIG. 6A, in accordance with an embodiment of the present specification. View 6000b illustrates an internal side of panel 6050, which is the side that faces main component portion of a multi-element tip cover of the endoscope. In the figure, placement of electronic board 6092 with side illuminators is shown within the panel 6050. The outer side of electronic board 6092 includes illuminator sets, of which only one set 6038 is visible in the figure. In embodiments, inner surface of electronic board 6092 includes electrical pads 6040 that connect to the illuminator sets on one side and are adapted to connect to leaf connectors on the other side. In embodiments, electronic pads 6040 are connected to the electronic board 6092 by VIAs—through holes, plated by copper. As stated earlier, the leaf connectors enable illuminator sets to interface with the power source which may be controlled through a main control box of the endoscope.

Figure 7A:
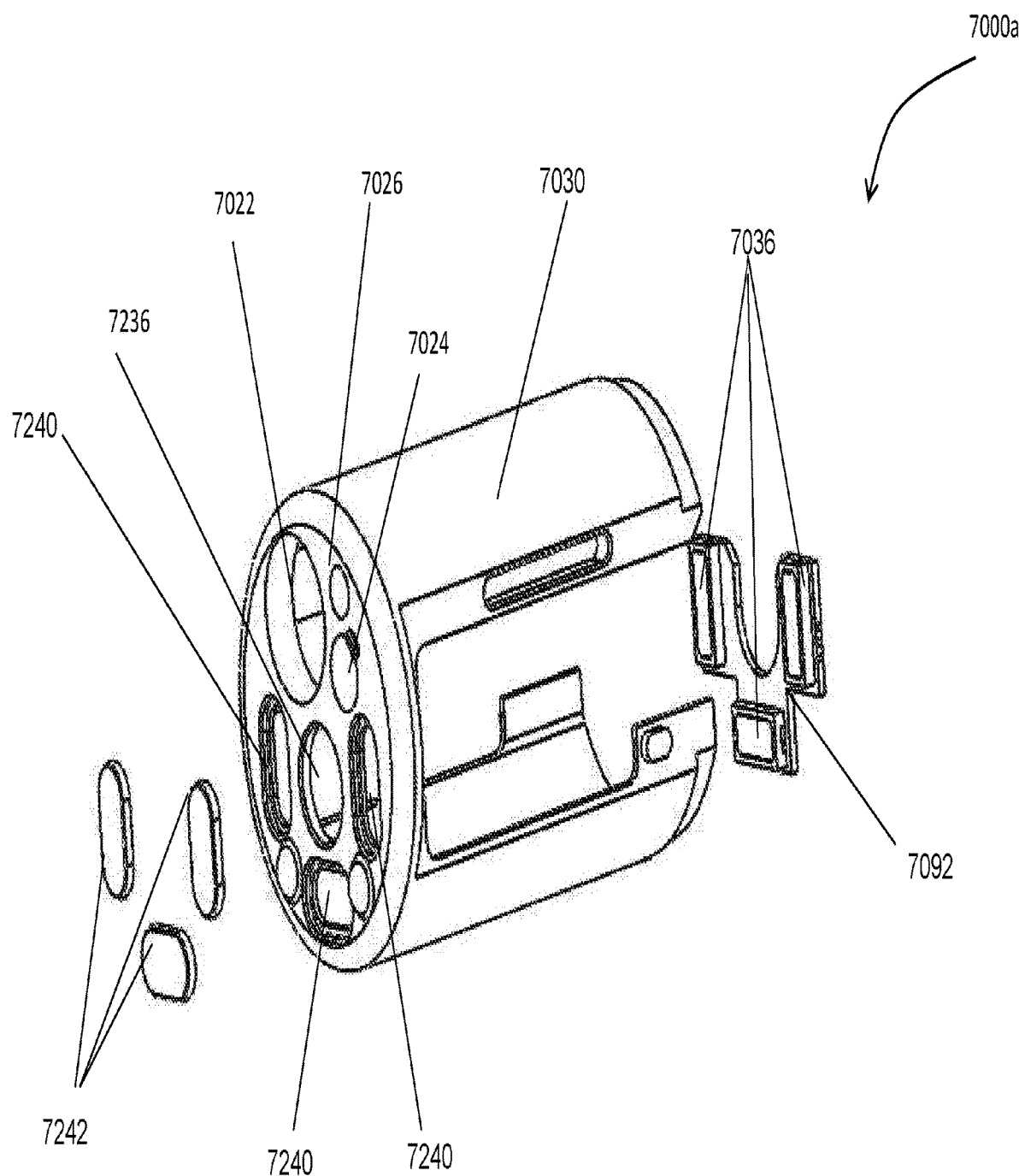
FIG. 7A is an isometric view of multi-element tip cover, in accordance with an embodiment of the present specification.

FIG. 7A illustrates an isometric view of multi-element tip cover 7000a, in accordance with an embodiment of the present specification. In this figure, side removable window component (shown as side removable window component 6050 in FIG. 6A) is removed. The figure also shows a front view of a main component portion 7030 of a multi-element tip cover 7000a. The front panel comprises a window or opening 7236 for a front optical lens assembly, openings 7240 for illuminators, a working/service channel opening 7022, a front nozzle opening 7024, and a front jet opening 7026. The figure illustrates three front illuminators openings 7240 and outer windows 7242. The outer windows 7242 may be placed over front illuminators openings 7240. In embodiments, illuminator sets 7036 are placed over a front illuminator electronic circuit board 7092, which illuminate through openings 7240 and illuminators' outer windows 7242. FIG. 7A illustrates front view of illuminator electronic circuit board 7092 when removed from the main component portion 7030. The figure shows three illuminator sets that are placed on three sides of the front viewing element in order to provide optimal illumination to the front viewing element assembly. In one embodiment, board 7092 is shaped as a 'U' and holds front illuminator sets 7036 in place.

Figure 7B:
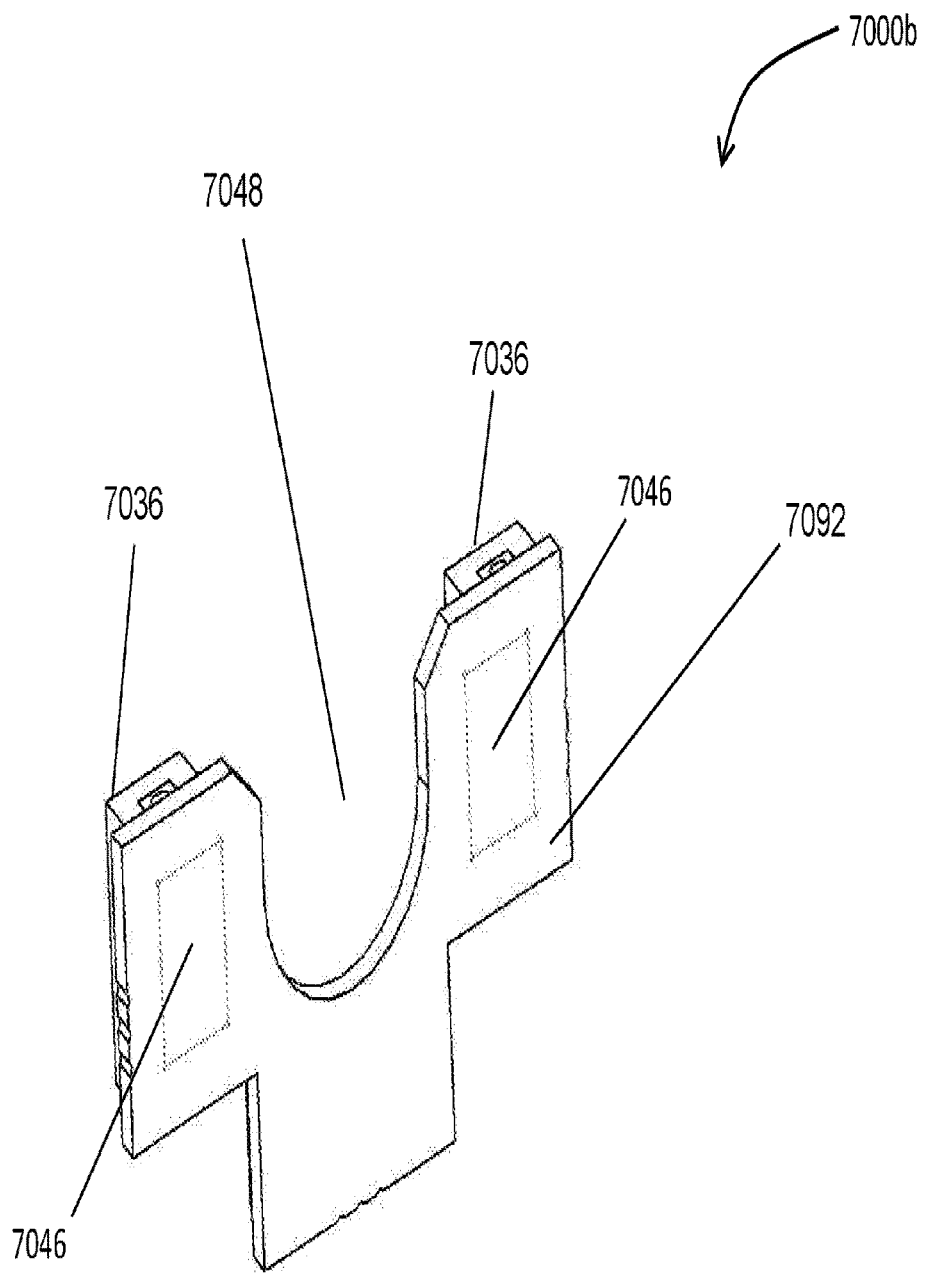
FIG. 7B is a rear view of a front illuminator electronic circuit board, revealing an internal side, in accordance with an embodiment of the present specification.

FIG. 7B illustrates a rear view 7000b of front illuminators electronic circuit board 7092, which reveals its internal side that faces away from the front panel, in accordance with an embodiment of the present specification. The front side of electronic board 7092 includes illuminator sets 7036, which are seen only partially in the present figure. In embodiments, inner surface of electronic board 7092 includes electrical pads 7046 that connect to illuminator sets 7036 on one side and are adapted to connect to leaf connectors (not shown) on the other side. In embodiments, pads 7046 are connected to board the 7092 by VIAs through holes, plated by copper. As stated earlier, the leaf connectors enable illuminator sets 7036 to interface with the power source, which may be controlled through a main control box of the endoscope. An opening 7048 in illuminators electronic circuit board 7092 is provided for the viewing element. In embodiments, opening 7048 is aligned with opening 7236 (shown in FIG. 7A).

Figure 8:
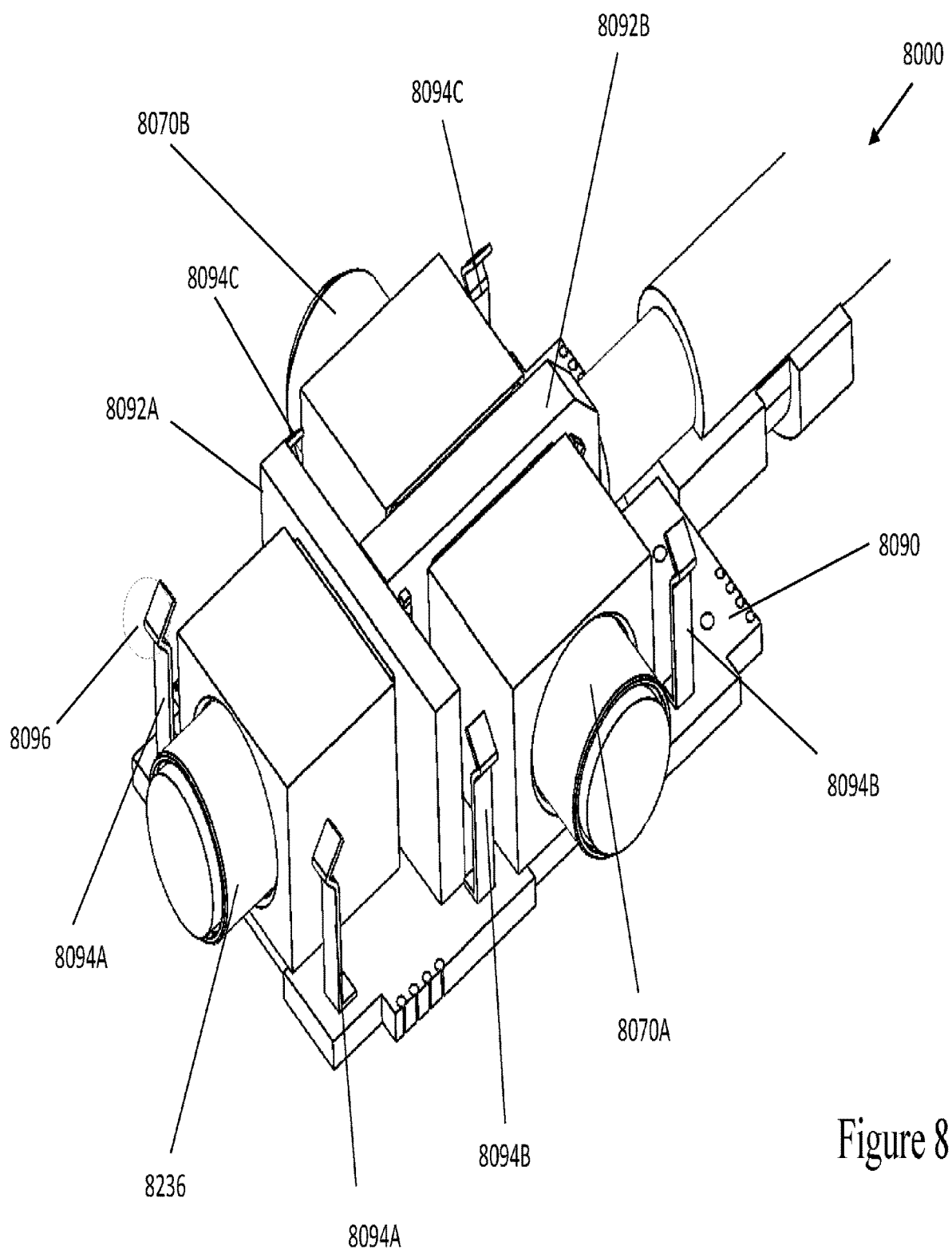
FIG. 8 illustrates an exemplary front top view of a base board assembly adapted to support the optical assembly and illuminators of an endoscope, in accordance with an embodiment of the present specification.

FIG. 8 illustrates an exemplary front top view of a base board assembly 8000 adapted to support the optical assembly and illuminators of an endoscope, in accordance with an embodiment of the present specification. Base board assembly 8000 comprises a main base board 8090, which is associated with two smaller baseboards—the front sensor base board 8092A and a side sensor base board 8092B. In one embodiment, front sensor base board 8092A and side sensor base board 8092B are placed perpendicular to each other. In one embodiment, front sensor base board 8092A and side sensor base board 8092B are also placed perpendicular to main base board 8090, in a three dimensional space. Front sensor base board 8092A carries the front sensor and front lens assembly 8236. Side sensor base board 8092B carries two side sensors and their associated side lens assemblies 8070A and 8070B. It may be noted that by placing the side sensors and lens assemblies on either side of the side sensor base board 8092B, the side sensors are able to share one board, thereby saving space in the endoscope tip. In an alternate embodiment, front sensor base board 8092A carries the front sensor and front lens assembly 8236, while side sensor base board 8092B carries only one side sensor and its associated side lens assembly 8070A or 8070B. In one embodiment, metal frames are positioned to support and hold the front and side lens assemblies 8236, 8070A, and 8070B. In an embodiment, metal frames may also serve as a heat sink to the sensors incorporated in the endoscope.

In one embodiment, separate leaf connectors are provided to connect to each electronic pad of the illuminator set, including the front illuminators set and side illuminators sets. The figure illustrates two leaf connectors 8094A for front illuminator sets of front optical assembly 8236, and two leaf connectors 8094B and 8094C for each of the side illuminator sets of side lens assemblies 8070A and 8070B. The number of leaf connectors may correspond to the number of illuminator sets that are provided with each optical assembly. In embodiments, leaf connectors 8094 are coupled to main base board 8090 by any suitable means, such as welding. A contact area 8096 between a leaf connector 8094 and a corresponding electronic pad (located on the illuminators electronic circuit board) is highlighted in a red circle. Each leaf connector 8094 comprises a similar contact area adapted to connect with the corresponding electronic pad of the electronic circuit board of illuminators sets, such as front illuminators electronic board 7092 of FIGS. 7A and 7B, and side illuminators electronic circuit board 6092 of FIGS. 6A and 6B. Contact area 8096 may be a rectangular strip, or a flat surface of any other shape that serves the purpose, such as but not limited to a square, a circle, and the like.

Figure 9:
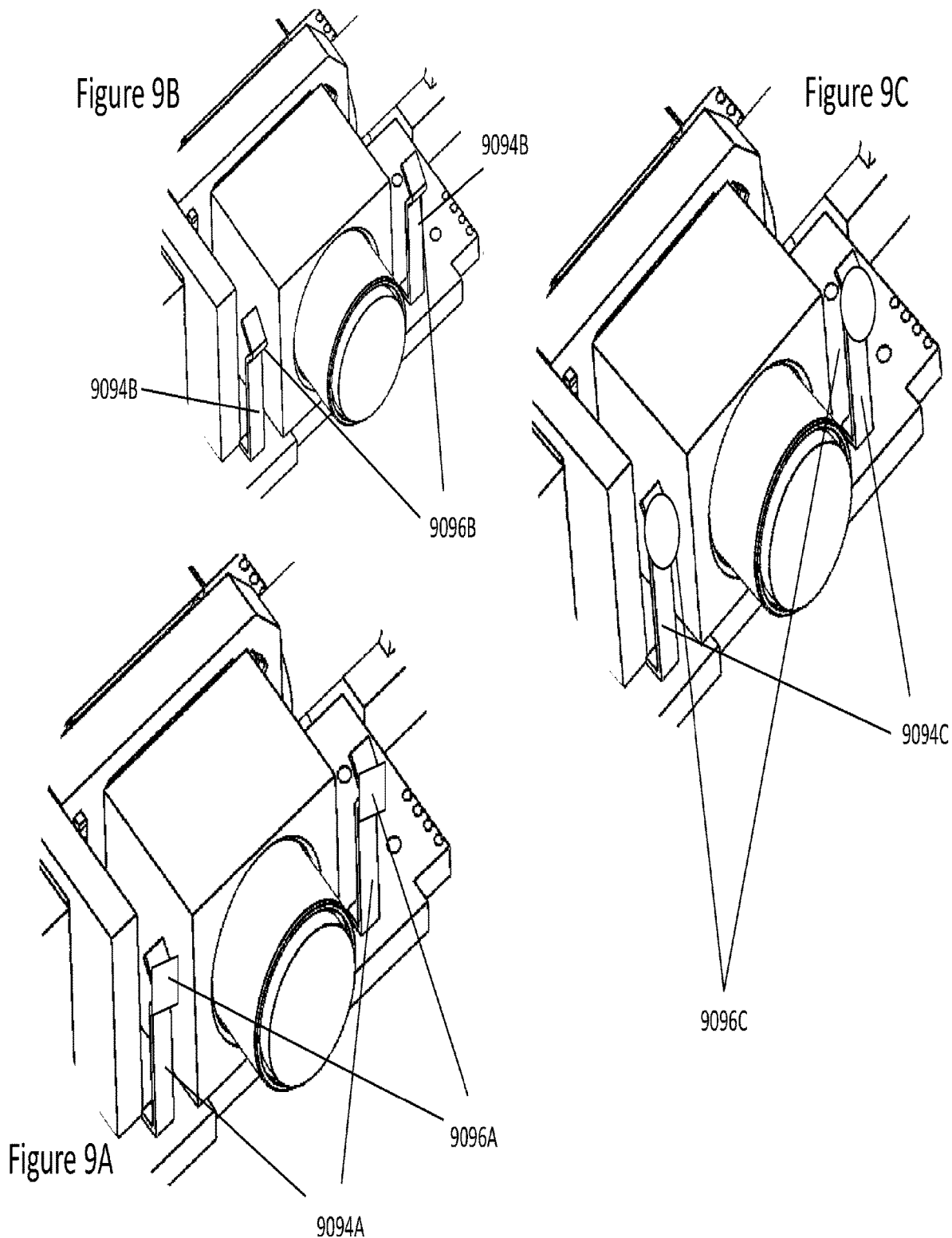
FIG. 9A shows a leaf connector comprising a square contact area, in accordance with an embodiment of the present specification.
FIG. 9B shows a leaf connector comprising a rectangular contact area, in accordance with an embodiment of the present specification.
FIG. 9C shows a leaf connector comprising a circular contact area, in accordance with an embodiment of the present specification.

FIGS. 9A, 9B, and 9C, illustrate various embodiments of leaf connectors 9094. FIG. 9A shows a leaf connector 9094A comprising a square-shaped contact area 9096A, in accordance with an embodiment of the present specification. FIG. 9B shows a leaf connector 9094B comprising a rectangular contact area 9096B, in accordance with an embodiment of the present specification. FIG. 9C shows a leaf connector 9094C comprising a circular contact area 9096C, in accordance with an embodiment of the present specification.

Figure 10:
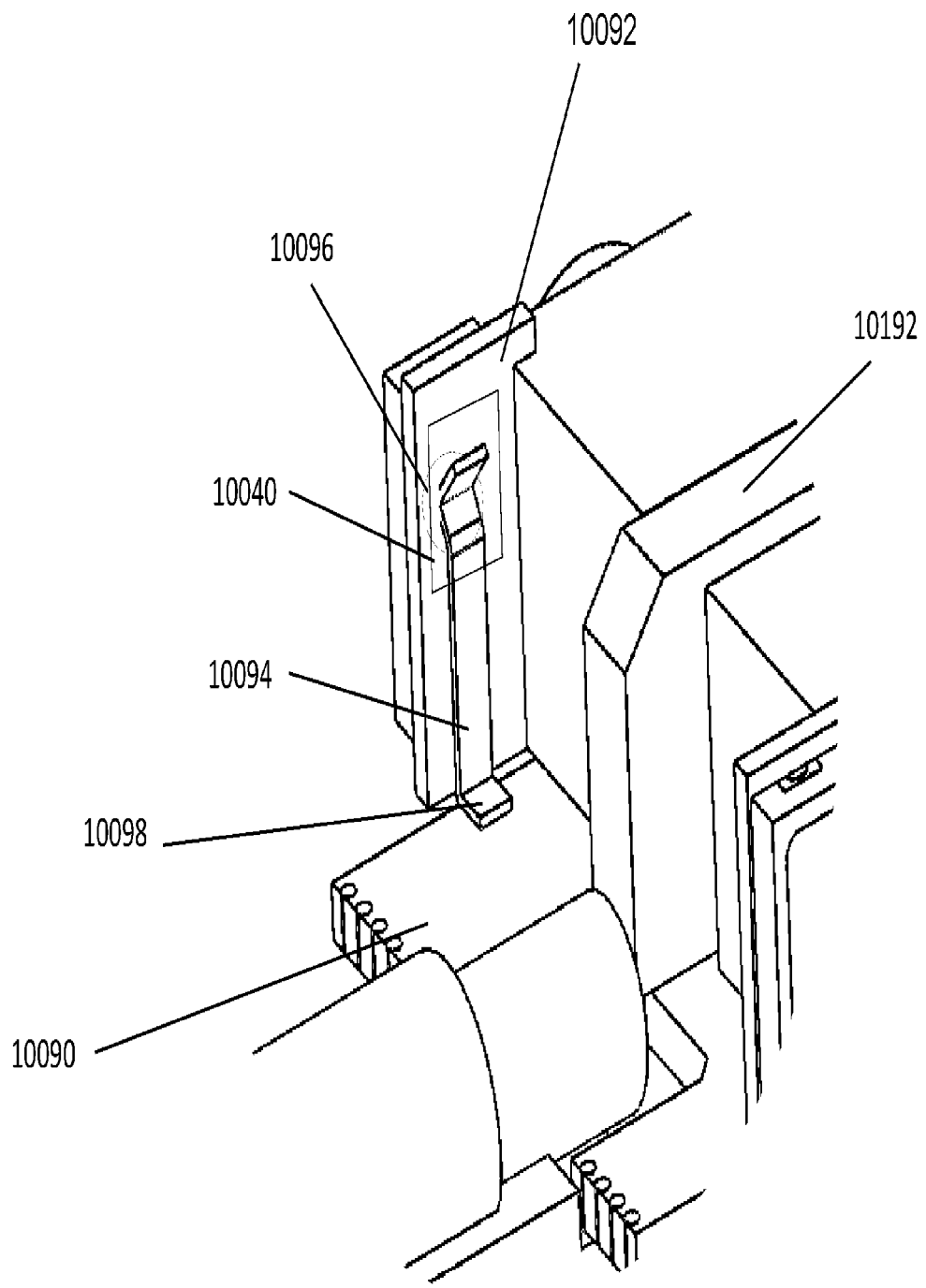
FIG. 10 illustrates a connection between an illuminator electronic circuit board and a contact area of a leaf connector, in accordance with an embodiment of the present specification; and, FIG. 11 illustrates an alternate embodiment for connecting an illuminator circuit board that utilizes a spring connector comprising a spring pin.

FIG. 10 illustrates a connection between an illuminators electronic circuit board 10092 and a contact area 10096 of a leaf connector 10094, in accordance with an embodiment of the present specification. Contact area 10096 connects to illuminators electronic circuit board 10092 over an electrical pad 10040 at a rear (inner) side of illuminators electronic circuit board 10092. Illuminators sets are attached to illuminators electronic circuit board 10092 on its other (outer) side. The figure shows connection 10098 between leaf connector 10094 and a main base board 10090, which may be a welded connection.

The figure also illustrates that illuminator electronic circuit board 10092 is placed parallel to a sensor base board 10192. In embodiments, sensor base board 10192 may be a front sensor base board or a side sensor base board, as described in context of FIG. 8. Similarly, illuminator electronic circuit board 10092 may be a front illuminator electronic circuit board when associated with the front sensor base board; and a side illuminator electronic circuit board when associated with a side sensor base board. In embodiments two side illuminator circuit boards are placed parallel on either side of a side sensor base board, in order to hold side illuminator sets associated with each of the side sensors/viewing elements.

Figure 11:
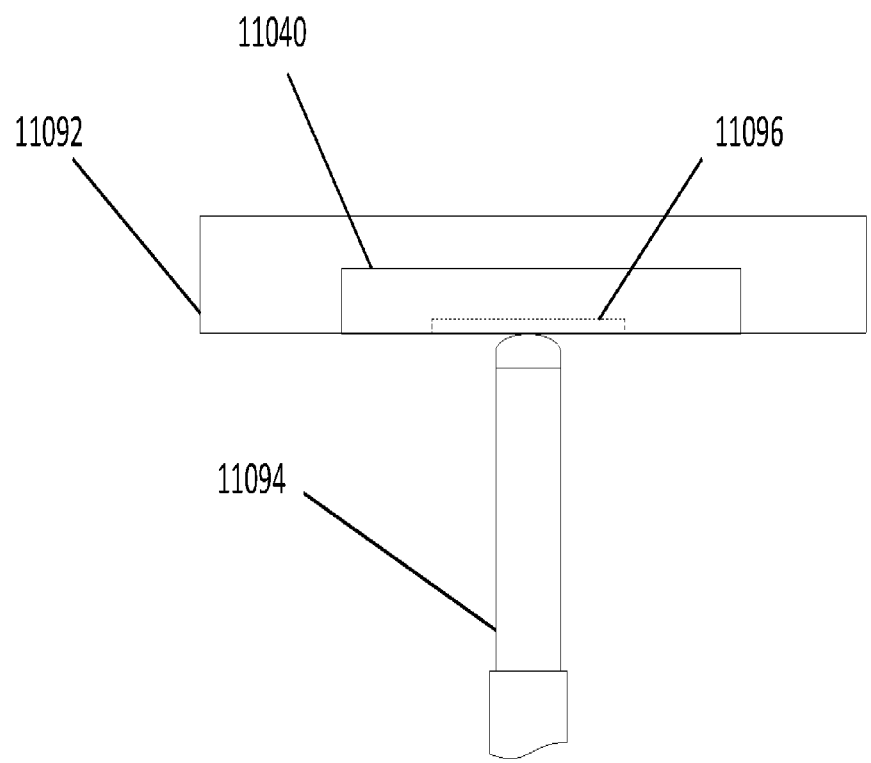

In alternative embodiments, a leaf connector may be replaced by a pitch spring-loaded right angle, horizontal SMT connector, or any other type of connector suitable for the various embodiments of the present specification. FIG. 11 illustrates one alternative embodiment that utilizes a spring connector comprising a spring pin 11094. In an embodiment, spring pin 11094 serves as a spring connector that touches an electrical pad 11040 over an area 11096. Electrical pad 11040 is attached to a rear (inner) side of an illuminators electronic circuit board 11092. Contact between spring pin 11094 and electrical pad 11040 enables a conductive extension from electrical pad 1104 to an illuminator that is attached to illuminators electronic circuit board 11092 on its other (outer) side.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A system for use in a medical device, the system comprising:
    a front viewing element;
    a side viewing element;
    a first circuit board connected to the front viewing element and the side viewing element;
    a cover comprising:
        a main component configured to cover a portion of a tip section of the medical device, the main component comprising a distal face and one or more side walls extending proximally from the distal face and extending longitudinally along a length of the tip section; and
        a removable window component located adjacent to the one or more side walls of the main component and entirely proximal of the distal face, wherein the removable window component includes a first window opening, and the removable window component is configured to removably cover a second window opening defined by the main component; and
    a second circuit board coupled to the removable window component.

2. The system of claim 1, wherein the second circuit board is U-shaped, and the first window opening is positioned between opposing portions of the second circuit board.

3. The system of claim 1, wherein the removable window component includes a recessed portion, and wherein the recessed portion defines the first window opening and a third window opening.

4. The system of claim 3, wherein the removable window component includes a third window opening configured to align with an illuminator and a fourth window opening configured to align with a liquid nozzle, wherein the first window opening is configured to align with the side viewing element.

5. The system of claim 1, wherein the removable window component includes a third window opening.

6. The system of claim 5, further comprising an illuminator coupled to the second circuit board, wherein the illuminator aligns with the third window opening.

7. The system of claim 1, wherein the second window opening extends to the proximal end of the main component and is formed by at least two edges of the main component extending parallel to a central longitudinal axis of the main component; and wherein the main component includes a third window opening facing a direction transverse to a direction the second opening faces.

8. The system of claim 1, wherein the second circuit board is coupled to a side of the removable window component facing the main component.

9. The system of claim 1, wherein the second circuit board includes electrical pads configured to couple to the first circuit board via one or more connectors.

10. The system of claim 9, wherein the one or more connectors are leaf connectors.

11. The system of claim 1, wherein the second window opening is defined by edges that are adapted to couple to the removable window component.

12. The system of claim 1, wherein the second window opening is aligned with at least one of:

the side viewing element;
    an optical assembly of the side viewing element;
    a side illuminator; and
    a side nozzle.

13. A system for use in a medical device, the system comprising:

a front viewing element;
    a side viewing element;
    a cover having a central longitudinal axis and comprising:

a main component configured to cover a portion of a tip section of the medical device, the main component comprising a distal face and one or more side walls extending proximally from the distal face and extending longitudinally along a length of the tip section; and a removable window component located adjacent to the one or more side walls of the main component and proximal of the distal face, the removable window component is configured to removably cover a first window opening defined by the main component, wherein an entirety of the removable window component is spaced from the central longitudinal axis; and a first circuit board coupled to a side of the removable window component facing the main component.

14. The system of claim 13, wherein said removable window component comprises a flat depression having a second window opening for accessing the side viewing element.

15. The system of claim 13, wherein a radially-outermost surface of the removable window component is curved.

16. The system of claim 13, wherein the removable window component includes at least two straight edges.

17. The system of claim 13, further comprising at least one illuminator coupled to the first circuit board.

18. The system of claim 13, further comprising at least one transparent or translucent window coupled to the removable window component and extending across at least one opening in the removable window component.

19. The system of claim 13, wherein the removable window component includes a second window opening, wherein the second window opening is aligned with at least one of:

the side viewing element;
    an optical assembly of the side viewing element;
    a side illuminator; and
    a side nozzle.

* * * * *